United States Patent [19]
Tanaka et al.

[11] Patent Number: 5,368,036
[45] Date of Patent: Nov. 29, 1994

[54] ULTRASOUND PROBE

[75] Inventors: Toshizumi Tanaka; Hiromu Itoi, both of Omiya, Japan

[73] Assignee: Fuji Photo Optical Co., Ltd., Omiya, Japan

[21] Appl. No.: 137,756

[22] Filed: Oct. 19, 1993

[30] Foreign Application Priority Data

Oct. 20, 1992 [JP] Japan .................................. 4-306235

[51] Int. Cl.⁵ .............................................. A61B 8/00
[52] U.S. Cl. .................................. 128/662.06; 128/4
[58] Field of Search ......... 128/4, 660.1, 662.05–662.06

[56] References Cited

U.S. PATENT DOCUMENTS

| | | | |
|---|---|---|---|
| 4,928,699 | 5/1990 | Sasai | 128/4 X |
| 4,957,112 | 9/1990 | Yokoi et al. | 128/4 X |
| 5,014,600 | 5/1991 | Krauter et al. | 128/4 X |
| 5,020,539 | 6/1991 | Yokoi et al. | 128/4 X |
| 5,248,989 | 9/1993 | Saiga et al. | 128/662.06 X |

*Primary Examiner*—Francis Jaworski
*Attorney, Agent, or Firm*—Oblon, Spivak, McClelland, Maier & Neustadt

[57] ABSTRACT

A joint construction for joining an end cap and a pliant sheathing tube of an ultrasound probe of type including a rigid tip member supporting thereon an ultrasound transducer element and housed in the end cap together with the ultrasound transducer element, and a flexible rotation transmission shaft connected at the fore end thereof to the tip member to transmit rotation thereto and fitted in the pliant sheathing tube. According to the invention, the joint construction further comprises a metal ring fixedly fitted in a fore end portion of the pliant sheathing tube by the use of an adhesive, the fore end portion of the pliant sheathing tube being in turn fixedly fitted in a joining base end portion of the end cap by the use of an adhesive to form overlapped end portions immediately around the metal ring, and a spooled thread portion tightly wound around the overlapped end portions of the end cap and pliant sheathing tube and anchored in position around the overlapped end portions by use of an anchoring adhesive.

12 Claims, 3 Drawing Sheets

ULTRASOUND PROBE

FIELD OF THE ART

This invention relates to an ultrasound probe to be inserted, for example, into an intracavitary portion of a human body for ultrasound examination, and more particularly to a joint construction for joining an end cap with a pliant tube sheathing the body of an ultrasound probe.

DESCRIPTION OF PRIOR ART

In the field of ultrasound examination systems, which are resorted to for examination of intracorporeal tissue conditions, it has become the general practice to employ, in addition to an external or percutaneous type ultrasound probe which is designed to transmit and receive ultrasound signals through the outer skin of a patient, an internal or insert type ultrasound probe to be inserted into an intracavitary portion of a patient to make a radial and/or linear scan along an intracavitary wall of interest while transmitting and receiving ultrasound signals. In turn, the insert type ultrasound probes has two types, i.e., a direction insertion type to be inserted directly into an intracavitary portion and an indirect insertion type to be inserted into an intracavitary portion, for example, under guidance of an endoscope or the like. In any case, an ultrasound transducer element is mounted on a rigid tip member which is connected to the fore end of a flexible insert cable.

For example, U.S. Pat. No. 5,131,393 discloses an insert type ultrasound probe which is designed to be used with an endoscope, utilizing as a guide a biopsy channel which is usually provided on an endoscope for insertion of forceps or other biopsy instruments. In this regard, in view of the narrowness of the biopsy channels of this sort, there has been a strong demand for ultrasound probes of reduced diameters which can guarantee easy insertion through such biopsy channels. For the same reason, a single element ultrasound transducer is usually employed for the ultrasound transducer to be mounted on the tip member at the fore end of the probe.

In order to permit ultrasound scanning operations, the cable which is connected to the tip member at the distal end of the probe is required to be able to transmit rotation to the ultrasound transducer on the tip member by remote control not only in radial scans but also in linear scans. This requirement can be met by the use of a flexible cable of double layer construction composed of a hollow flexible shaft consisting of a number of rotation transmitting members like tightly wound coil springs, which are arranged in multiple parallel rows or in multiple layers and sheathed in an elastic or pliant tube. A cable of signal lines to and from the ultrasound transducer is passed through the hollow center space of the flexible rotation transmission shaft.

The pliant sheathing tube which covers the flexible shaft is preferred to be of a slippery or friction-free material in order to ensure smooth rotation of the internal flexible shaft and smooth insertion of the ultrasound probe exactly to a point of interest or a point of examination not only in case of direct insertion but also in case of indirect insertion through a biopsy channel of an endoscope or the like. Therefore, it has been the general practice to employ a fluorine-contained resin or the like for the sheathing tube.

The ultrasound transducer element which is mounted on the tip member is invariably subjected to contaminations or damages if it is retained in an exposed state. Besides, it is very probable that an intracavitary wall portion which is in contact with the rigid tip member be scratched or caught by the tip member especially in case of radial scans where the rigid tip member is put in rotation. In order to prevent these troubles, the rigid tip member is usually housed in an end cap which is fixedly connected at its inner base end to the pliant sheathing tube of the insert cable. This means that the ultrasound signals which are transmitted and received by the ultrasound transducer are always passed through the end cap. Therefore, for the purpose of suppressing attenuation of ultrasound signals to a minimum, it is desirable that the end cap be formed of a material with satisfactory acoustic characteristics, and an ultrasound transmissive medium like fluid paraffin be sealed in the end cap. Accordingly, the end cap is normally formed of hard polyethylene, polyimide, vinyl chloride, epoxy resin, urethane resin or the like. In this regard, the fluorine-contained resin, which is suitably used for the sheathing tube, is undesirable from the viewpoint of acoustic characteristics.

Since the end cap needs to be formed of a material of a different nature as compared with that of the pliant sheathing tube, which constitutes the outermost skin layer of the ultrasound probe as mentioned above, it is extremely difficult to form these parts as one integral part. Therefore, the pliant sheathing tube and end cap need to be fixedly joined with each other, normally by the use of a joint ring member. For example, joining ends of a pliant sheathing tube and an end cap are fitted on a joint ring from the opposite ends thereof and bonded to the latter by the use of an adhesive. Alternatively, joining ends of an end cap and a pliant sheathing tube are fitted on the outer and inner peripheries of a joint ring of a stepped form, respectively, followed by bonding fixation by the use of an adhesive. In most cases, such a joint ring is made of a metallic material in consideration of shape retainability and strength of the adhesive bond. Besides, each joint ring is required to have a substantial length in the axial direction, including a length for fitting engagement with the joining end of an end cap plus a length for fitting engagement with the joining end of a pliant sheathing tube.

No matter whether the direct insertion type to be inserted directly into an intracavitary portion or the indirect insertion type to be inserted with aid of a guide means like an endoscope, the ultrasound probe is invariably required to be able to bend itself as it is introduced along a path of insertion leading to an intracavitary portion of interest. Especially in the case of an ultrasound probe to be inserted under the guidance of an endoscope, it is flexed to a greater degree at an angle section at the fore end of the insert portion of the endoscope if the angle section is in a bent state. The flexures of this nature often jeopardize the conditions of the adhesive bond between the joint ring and the pliant sheathing tube which is made of a slippery material as mentioned above. In addition, the bending force applied across the bond between the pliant sheathing tube and joint ring tends to bend part of the sheathing tube inward and thus tends to detach the pliant sheathing tube from the joint ring, further deteriorating the strength of the bond between these parts. Accordingly, repeated application of such bending forces to the bonded area will result in loosening of the bond, finally causing the end cap to fall apart from the pliant sheathing tube.

Further, if the bonding area is increased to an extent which would be sufficient for precluding the loosening problem of the adhesive bond between the joint ring and pliant sheathing tube, the rigid portion at the fore end of the ultrasound probe will become too lengthy and will present itself as an obstacle at the time of probe inserting operations, coupled with a problem that, when a given bending force is imposed, the pliant sheathing tube is caused to bend to a greater degree relative to the joint ring, accelerating the loosening of its bond to the joint ring.

Further, the joint ring which is made of a metal is normally electrically conductive. In this regard, considering the nature of the ultrasound transducer element to which electric signals are transmitted, any metal part which is exposed on the outer side of the insert portion of the probe, to be introduced into an intracavitary portion, should be electrically insulated from the power source for safety purposes. Of course, initially there is almost no possibility of a metal joint ring being brought into direct contact with an intracavitary wall as long as the pliant sheathing tube and end cap are fitted and bonded on the outer periphery of the joint ring in such a manner as to cover up the joint ring completely. However, loosening of the adhesive bond progresses by repeated use of the probe, making it difficult to prevent completely direct contact of the metal ring with intracavitary wall portions under examination.

SUMMARY OF THE INVENTION

With the foregoing problems or difficulties in view, the present invention has as its object the provision of a joint construction for securely joining an elastic or pliant sheathing tube of an ultrasound probe with an end cap fitted at the tip end of the ultrasound probe, in such a manner as to shorten the length of a rigid portion at the fore end of the probe while securely preventing the end cap from falling apart from the pliant sheathing tube.

According to the present invention, the above-stated objective is achieved by the provision of a joint construction for joining an end cap and a pliant sheathing tube of an ultrasound probe of the type including a rigid tip member supporting thereon an ultrasound transducer element and housed in the end cap together with the ultrasound transducer element, and a flexible rotation transmission shaft connected at the fore end thereof to the tip member to transmit rotation thereto and fitted in the pliant sheathing tube, characterized in that the joint construction comprises a metal ring fixedly fitted in a fore end portion of the pliant sheathing tube by the use of an adhesive, the fore end portion of the pliant sheathing tube being in turn fixedly fitted in a joining base end portion of the end cap by the use of an adhesive to form overlapped end portions immediately around the metal ring, and a spooled thread portion tightly wound around the overlapped end portions of the end cap and pliant sheathing tube and anchored in position on the overlapped end portions by the use of an adhesive.

DESCRIPTION OF PREFERRED EMBODIMENTS

Figure 1:
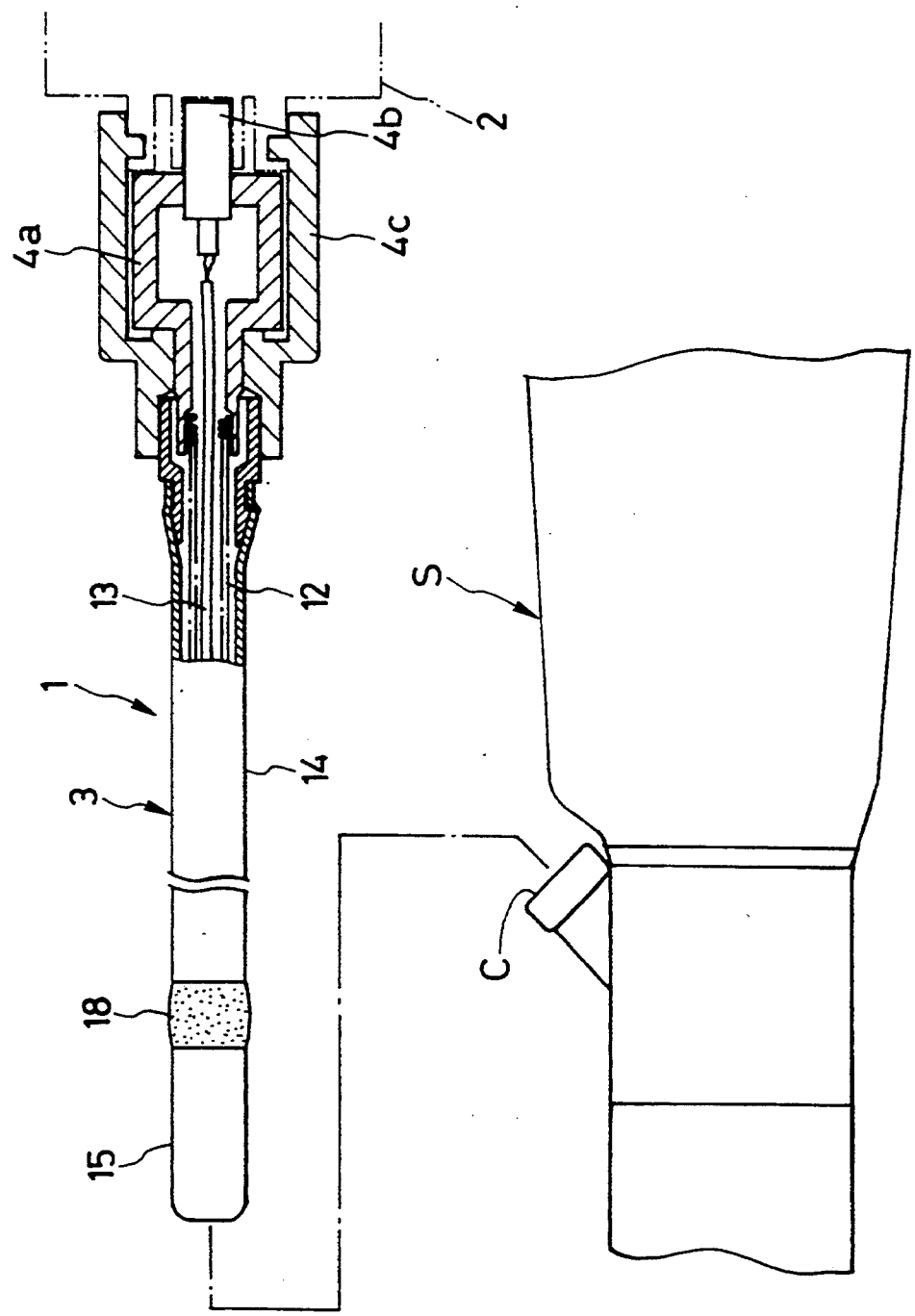
FIG. 1 is a fragmentary, partly sectioned view of an ultrasound probe in an embodiment of the present invention, showing the general construction of the probe.

Hereafter, the invention is described more particularly by way of its preferred embodiments shown in the drawings.

Figure 2:
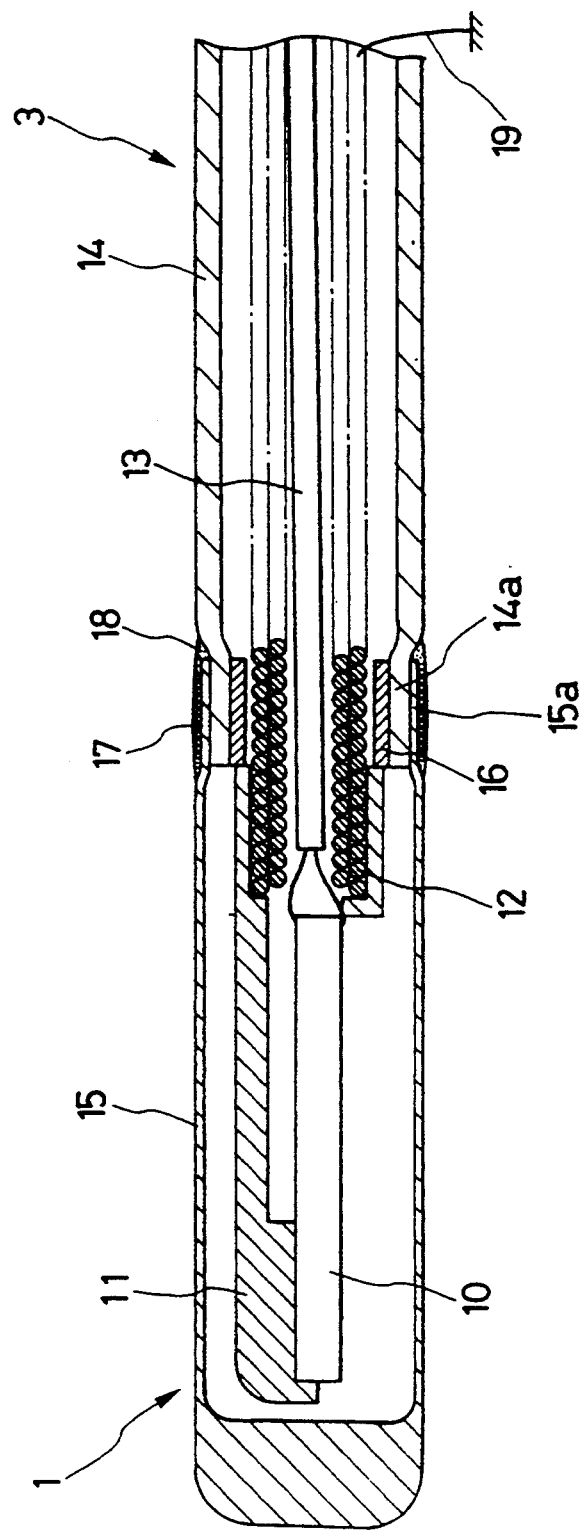
FIG. 2 is a longitudinal sectional view on an enlarged scale of a fore end portion of the probe of FIG. 2.

Referring to FIGS. 1 and 2, indicated at 1 is an ultrasound probe, and at 2 is an operating unit for the ultrasound probe 1. The ultrasound probe 1 is generally composed of a probe proper 3 and a connector 4 to be coupled with the operating unit 2 which contains a rotational drive means like an electric motor. When the connector 4 is coupled with the operating unit 2, the probe can perform a radial scan upon actuating the rotational drive means on the operating unit 2. Alternatively, for and at the time of a linear scan, the probe 3 proper is displaced in the axial direction. The ultrasound probe 1 is adapted to be introduced into an intracavitary portion of interest through an entrance opening C of a biopsy channel which is provided on an endoscope S for insertion of forceps or other instruments, and operated through the operating unit 2 for either a radial or linear scan.

Denoted at 10 is an ultrasound transducer element for transmission and reception of ultrasound signals. The ultrasound transducer element 10 is fixedly mounted on a rigid tip member 11 which is connected to the fore end of a flexible rotation transmission shaft 12. The rear or base end of the flexible shaft 12 is connected to a rotary member 4a on the connector 4. In order to transmit the rotation of the rotary member 4a to the tip member 11, the flexible shaft 12 is constituted by a number of tightly wound coil springs which are arranged in multiple parallel rows or in multiple layers. A signal cable 13 is connected to the ultrasound transducer element 10 for applying trigger signals to the transducer element 10 while transferring received echo signals to an ultrasound image observation unit which is not shown. The signal cable 13 is passed longitudinally through the hollow flexible shaft 12 and is connected to an electric connector member 4b of the connector 4.

The flexible shaft 12 is in turn sheathed in an elastic or pliant tube 14, the base end of which pliant sheathing tube 14 being connected to a cap member 4c of the connector 4, which is non-rotatably fixed on the casing of the operating unit 2. The other or the fore end of the pliant sheathing tube 14 is disposed rotatably relative to both the flexible shaft 12 and the tip member 11. The fore end of the pliant sheathing tube 14 is connected to an end cap 15 which accommodates the tip member 11.

With the above-described arrangements according to the invention, the ultrasound probe 1 is introduced, through the biopsy channel of the endoscope S, into a position close to an intracavitary wall portion to be examined. In this state, the ultrasound probe 1 is scanned in a linear direction or in a radial direction while transmitting ultrasound pulse signals at predetermined time intervals toward the intracavitary wall under observation and at the same time receiving reflected echo signals through the ultrasound transducer element 10. The received echo signals are fed through the signal cable 13 to the ultrasound image observation terminal to undergo predetermined signal processing there to produce on a monitor an ultrasound image which gives tomographic information on tissues of the intracavitary wall under observation.

Needless to say, the tip member 11 which carries the ultrasound transducer element 10 needs to be rotationally driven in radial scan operations. However, even in linear scan operations, there often arises a need for turning the tip member 11 in order to adjust the direction of the active face of the ultrasound transducer element 10. The directional adjustment of the ultrasound transducer element 10 becomes necessary also in examinations in M-mode or by Doppler's method. In this regard, the flexible shaft 12 which is fitted in the pliant sheathing tube 14 is restrained of deflective movements, so that, upon turning the flexible shaft 12 about its axis by the rotational drive means on the operating unit 2 or by manual efforts, its rotation is smoothly and securely transmitted to the tip member 11.

For the purpose of permitting smooth sliding movement of the flexible rotation transmission shaft 12 in the sheathing tube 14, and for ensuring smooth insertion of the ultrasound probe 1 into the biopsy channel of the endoscope S through the entrance C, the pliant sheathing tube 14 is formed of a material with extremely slippery surfaces, for example, a fluorine-contained resin. In contrast, considering that the ultrasound signals are transmitted and received through the end cap 15, it is a paramount requirement to form the end cap 15 from a material with excellent properties in transmittance of ultrasound signals, namely, with excellent acoustic characteristics, along with suitable electric insulating properties. Accordingly, the end cap 15 is preferably formed of a synthetic resin material with satisfactory acoustic characteristics like hard polyethylene. In this regard, polyimide, vinyl chloride, epoxy resin, urethane resin can also be adopted. However, the fluorine-contained resin, selected for the pliant sheathing tube 14, is unsuitable for the end cap 15 from the standpoint of acoustic characteristics.

Thus, the pliant sheathing tube 14 and the end cap 15 are formed of different materials and are subsequently joined together in the manner as described below. A base end portion of the end cap 15 is directly fitted on a fore end portion of the pliant sheathing tube 14, and their overlapped end portions are securely bonded to each other by means of an adhesive. In this instance, preferably the overlapped end portions 14a and 15a of the pliant sheathing tube 14 and end cap 15 are reduced in thickness to a certain extent to prevent the probe from bulging out to have a markedly increased outside diameter at the overlapped end portions which will form a joint portion. However, both of the end cap 15 and the pliant sheathing tube 14 are formed of a resilient material, so that, in this simply bonded state, they are susceptible to deformations or loosening of the adhesive bond when a pressure is imposed from outside. In order to impart suitable strength against deforming or crushing forces, a metal ring 16 is fitted in the pliant sheathing tube 14 before bonding the same with the end cap 15, at a position to be located immediately on the inner side of the overlapped end portions of the pliant sheathing tube 14 and the end cap 15. The metal ring 16 is fixedly bonded to the inner periphery of the pliant sheathing tube 14 by means of an adhesive or the like. Further, a spooled thread portion 17 is provided around the overlapped end portions of the sheathing tube 14 and the end cap 15, by tightly winding a thread in such a manner as to clamp the overlapped end portions to each other and to the metal ring 16. The spooled thread portion 17 is securely cemented or anchored in position on the overlapped end portions or the joint portion by the use of an adhesive 18. The spooled thread portion 17 and the anchoring adhesive 18 are applied until the edge of the overlapped end portion of the end cap 15 is completely covered up, for securely holding the bond between the overlapped end portions and at the same time preventing the end cap 15 from getting loose from a raveled edge portion. The overlapped end portions are made thinner than other portions as mentioned before, so that they provide a shallow groove in which the spooled thread 17 and adhesive 18 can nest substantially in a flat state. Consequently, the ultrasound probe 1 presents uniform shape and thickness along its entire length without ups and downs.

The pliant sheathing tube 14 can freely bend itself and has very slippery surfaces as described above. Therefore, when a fore end portion of the probe 1 is bent or warped, it is probable that the sheathing tube 14 be deformed easily to such a degree as to cause loosening of the adhesive bond of the pliant sheathing tube. However, the overlapped end portions of the pliant sheathing tube 14 and the end cap 15 are immune to such loosening of the bond as they are tightly fastened to each other by and between the metal ring 16 and the spooled thread portion 17 on the inner and outer sides of the overlapped end portions. Especially, by tightly winding the thread in the spooled thread portion 17, the pliant sheathing tube 14 and the end cap 15, each formed of a resilient synthetic resin material, are clamped to each other with a very strong pressing force which implements the strength of the bond all the more. Besides, the metal ring 16 on the inner side of the overlapped end portions serves to retain the shape of the joint portion even if the spooled thread 17 is tightened to a maximum degree, and to protect the joint portion against crushing forces.

Except for the hard end cap 15 which houses the tip member 11 and the ultrasound transducer element 10, the ultrasound probe 1 has to be able to bend itself freely along a path of insertion. In other words, the axial length of the rigid portion at the fore end of the probe, including the end cap 15, should be as small as possible. Therefore, a rigid joint portion provided between the end cap 15 and the pliant sheathing tube 14 could be an obstacle to the operability of the ultrasound probe at the time of insertion through a biopsy channel of an endoscope. However, according to the present invention, the rigid metal ring 16 exists only under the overlapped end portions of the end cap 15 and the pliant sheathing tube 14, that is to say, the rigid portion is restricted substantially to the length of the end cap 15 itself to ensure high operability of the probe at the time of insertion thereof.

Further, with the above-described ultrasound probe 1, only the end cap 15 and the pliant sheathing tube 14 are exposed on the outer side of the probe body except the spooled thread portion 17 and the anchoring adhesive 18. All of these exposed portions are formed of a synthetic resin material with excellent insulating properties in terms of safeguard of patients and prevention of production of noises which would interfere with signals to and from a solid-state image sensor device in case the ultrasound probe is used together with an electronic endoscope. In addition, the joint portion has a quadruple layer construction, namely, the metal ring 16 which forms the innermost layer of the joint portion is covered under a first layer formed by the spooled thread 17 and the anchoring adhesive 18, a second layer formed by the end cap 15 and a third layer formed by the pliant sheathing tube 14, which all have electric insulating properties and completely preclude the possibility of the metal ring 16 directly contacting intracavitary wall portions of a patient. For the purpose of improving shielding effects, the flexible shaft 12, which is normally made of a metallic material, may be maintained at the ground potential by way of a grounding wire 19 connected thereto. This will permit reducing noises in input and output signals of a solid-state image sensor device to a marked degree.

The joint portion of the probe, which has the overlapped end portions of the pliant sheathing tube 14 and end cap 15 sandwiched between the inner metal ring 16 and the outer spooled thread portion 17, necessarily becomes thicker than other portions of the probe. The sheathing tube 14 and end cap 15 are reduced in thickness at the respective overlapped end portions 14a and 15a as described hereinbefore. However, such reductions in thickness are limited in order to secure necessary strength of the sheathing tube 14 and end cap 15. On the other hand, if the joint portion bulges out to a conspicuous degree, it would hinder smooth insertion of the probe. To avoid this, the metal ring 16 is necessarily protruded radially inward, and as a result the internal space of the probe is constricted at the joint portion of the pliant sheathing tube 14 and the end cap 15 in an advantageous manner as described below.

Namely, when the flexible shaft 11 which consists of tightly wound coil springs is turned about its axis to rotationally drive the tip member 11, the coil springs tend to contract in the axial direction, pulling the tip member 11 toward them or in a direction away from the tip end of the probe. As a consequence, if in a free state, the ultrasound transducer element 10 on the tip member 11 is forcibly pulled in the axial direction during a radial scan. However, the metal ring 16 which is projected radially inward at the joint portion can function as a positioning member which delimits axial displacement of the tip member 11. More specifically, even if the tip member 11 is pulled by a contracting force of the flexible shaft 12, its axial movement toward the flexible shaft 12 is blocked by abutting engagement of peripheral edge portions at its inner or base end, which is connected to the flexible shaft 12, against the front end face of the metal ring 16.

Figure 3:
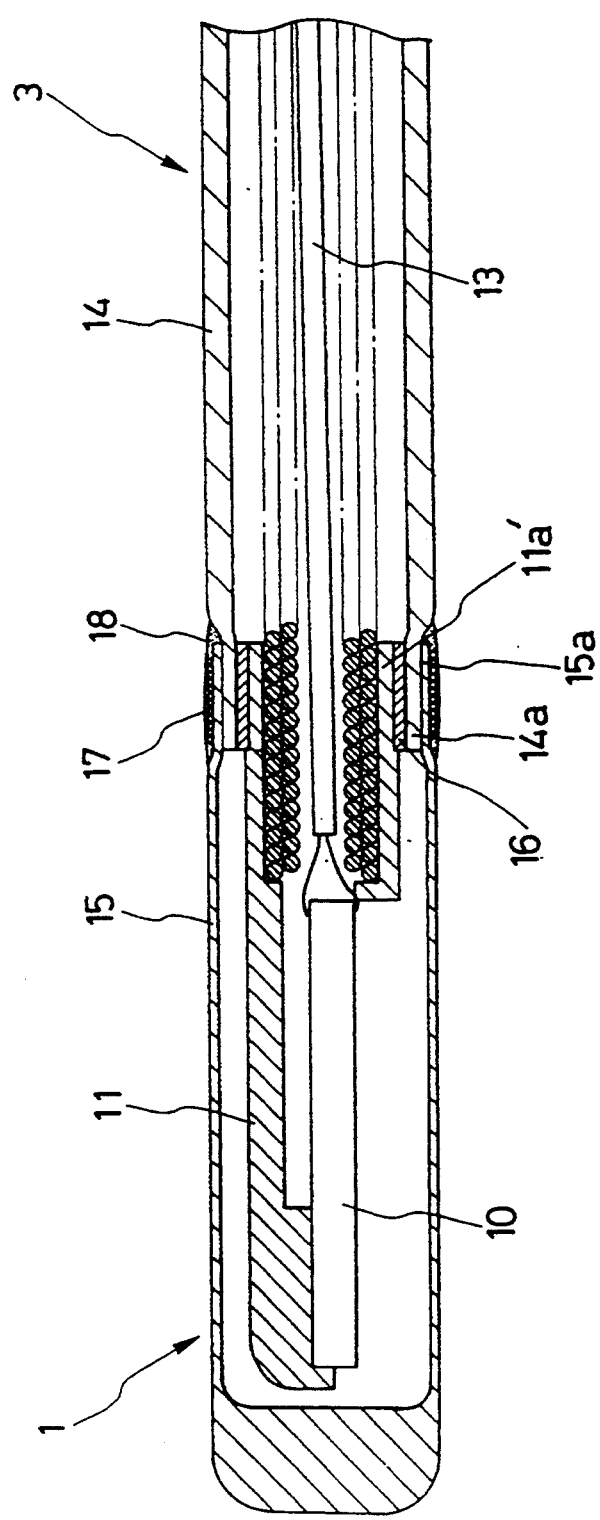
FIG. 3 is a view similar to FIG. 2 but showing a fore end portion of an ultrasound probe in another embodiment of the invention.

Further, in radial scan operations, deflective movements of the axis of rotation of the tip member 11 make accurate scanning operations impossible. In order to preclude this sort of problem, it is preferred to provide a smaller diameter portion 11a' at the base end of the tip member 11' as shown in FIG. 3, and to extend the smaller diameter portion 11a' through the metal ring 16 and connect it to the flexible shaft 12. The smaller diameter portion 11a' is dimensioned to have an outside diameter which is slightly smaller than the inside diameter of the metal ring 16, so that it can rotate substantially in sliding contact with the inner periphery of the metal ring 16. With this arrangement, the front end face of the metal ring 16 functions to block axial displacements of the tip member 11', while its inner peripheral surface functions to prevent deflective movements of the axis of rotation of the tip member 11', always ensuring a stable and accurate radial scanning operation.

In the foregoing embodiments, the invention has been explained by way of the ultrasound probe 1 to be inserted through a biopsy channel of an endoscope. However, it is to be understood that the present invention can be applied to an ultrasound probe which is designed to be independently and directly inserted into an intracavitary portion or into a blood vessel which needs an examination. Further, the present invention can be similarly applied to ultrasound probes of dual scan mode type capable of radial and linear scans or a single mode type capable of either a radial or linear scan, or to ultrasound probes of the electronical scan type.

What is claimed is:

1. An ultrasound probe of the type including a rigid tip member supporting thereon an ultrasound transducer element, a flexible rotation transmission shaft connected to said tip member to permit remote-control rotational drive of said ultrasound transducer element on said tip member, a pliable sheathing tube formed of a slippery soft material and fitted around said flexible shaft, an end cap formed of a material with suitable acoustic characteristics for transmission and reception of ultrasound signals therethrough and housing therein said ultrasound transducer element together with said tip member, said end cap having a base end portion thereof adhesively connected to said pliable sheathing tube in directly overlapped relation with a fore end portion of the pliable sheathing tube through a joint structure comprising:
   a metal ring fixedly fitted on an inner side of overlapped end portions of said pliable sheathing tube and end cap;
   a spooled thread portion wrapped on and around said overlapped end portions of said pliable sheathing tube and end cap to fasten said overlapped end portions to each other and to said metal ring; and
   an adhesive applied on an outer side of said overlapped end portion to anchor said spooled thread portion in position on a circumference of said overlapped end portions.

2. An ultrasound probe as defined in claim 1, wherein said pliable sheathing tube, end cap, spooled thread portion and anchoring adhesive are all formed of an electrically insulating material.

3. An ultrasound probe as defined in claim 1, wherein said flexible rotation transmission shaft is formed of a number of tightly wound coil springs arranged in multiple parallel rows or in multiple layers, and which are grounded.

4. An ultrasound probe as defined in claim 1, wherein said pliable sheathing tube and end cap are reduced in thickness at said overlapped end portions to nest said spooled thread portion and said anchoring adhesive substantially in a flat state.

5. An ultrasound probe as defined in claim 1, wherein said metal ring has an inside diameter smaller than the outside diameter of said tip member, and functions as a stopper blocking axial movement of said tip member.

6. An ultrasound probe as defined in claim 5, wherein said tip member is formed in a stepped form at the base end thereof and has a reduced diameter portion slidably fitted in said metal ring.

7. An ultrasound probe comprising:
   a rigid tip member supporting thereon an ultrasound transducer element;
   a flexible rotation transmission shaft connected to said tip member to permit rotation drive of said ultrasound transducer element on said tip member;
   a pliable sheathing tube fitted around said flexible shaft;

an end cap formed for transmission and reception of ultrasound signals therethrough and housing therein said ultrasound transducer element together with said tip member;

a joint structure for connecting the pliable sheathing tube to the end cap comprising:

a metal ring fixedly fitted on an inner side of overlapped end portions of said pliable sheathing tube and end cap;

a spooled thread portion wrapped on and around said overlapped end portions of said pliable sheathing tube and end cap to fasten said overlapped end portions to each other and to said metal ring; and an adhesive applied on an outer side of said overlapped end portions to anchor said spooled thread portion in position on a circumference of said overlapped end portions.

8. An ultrasound probe as defined in claim 7, wherein said pliable sheathing tube, end cap, spooled thread portion and anchoring adhesive are all formed of an electrically insulating material.

9. An ultrasound probe as defined in claim 7, wherein said flexible rotation transmission shaft is formed of a number of tightly wound coil springs arranged in multiple parallel rows or in multiple layers, and which are grounded.

10. An ultrasound probe as defined in claim 7, wherein said pliable sheathing tube and end cap are reduced in thickness at said overlapped end portions to nest said spooled thread portion and said anchoring adhesive substantially in a flat state.

11. An ultrasound probe as defined in claim 7, wherein said metal ring has an inside diameter smaller than the outside diameter of said tip member, and functions as a stopper blocking axial movement of said tip member.

12. An ultrasound probe as defined in claim 11, wherein said tip member is formed in a stepped form at the base end thereof and has a reduced diameter portion slidable fitted in said metal ring.

* * * * *